United States Patent [19]

D'Alterio et al.

[11] Patent Number: 5,270,194
[45] Date of Patent: Dec. 14, 1993

[54] STABILIZED GLUCOSE OXIDASE FROM ASPERGILLUS NIGER

[75] Inventors: Maurizio D'Alterio, Brugherio; Dario Frontini, Milan, both of Italy

[73] Assignee: Instrumentation Laboratory SpA, Milan, Italy

[21] Appl. No.: 948,062

[22] Filed: Sep. 18, 1992

Related U.S. Application Data

[63] Continuation of Ser. No. 575,075, Aug. 30, 1990, abandoned.

[30] Foreign Application Priority Data

Aug. 31, 1989 [IT] Italy .................. 21592 A/89

[51] Int. Cl.$^5$ .................. C12N 9/96; C12N 9/04; C12N 1/00; C12N 1/14
[52] U.S. Cl. .................. 435/188; 435/190; 435/917; 435/254.3
[58] Field of Search ............. 435/188, 190, 917, 254.3

[56] References Cited

U.S. PATENT DOCUMENTS

| | | | |
|---|---|---|---|
| 3,595,755 | 7/1971 | Härtel | 435/25 |
| 3,645,851 | 2/1972 | Bergmeyer et al. | 435/190 |
| 3,950,133 | 4/1976 | Monte et al. | 435/188 |
| 4,080,262 | 3/1978 | Beaucamp et al. | 435/188 |
| 4,444,878 | 4/1984 | Paulus | 435/188 |
| 4,537,764 | 8/1985 | Pellico et al. | 435/190 |

FOREIGN PATENT DOCUMENTS 0182225  5/1986  European Pat. Off. .

OTHER PUBLICATIONS

Rolf D. Schmid, "Stabilized Soluble Enzymes", Adv. Biochem. Eng. vol. 12, pp. 42-108 (1979).

Primary Examiner—David M. Naff
Assistant Examiner—Michael V. Meller
Attorney, Agent, or Firm—Testa, Hurwitz & Thibeault

[57] ABSTRACT

An aqueous liquid composition is disclosed. The composition comprises a stabilized glucose oxidase solution having a pH of from about 6.0 to 8.0 and contains phosphate at a concentration of 1500 to 2500 mM/l. The glucose oxidase retains at least 80% of its activity after 10 days at 37° C. The glucose oxidase is preferably derived from *Aspergillus niger*, has a concentration of from about 5 to about 50 IU/ml and a pH range of from about 7.1 to about 7.3.

4 Claims, 5 Drawing Sheets

STABILIZED GLUCOSE OXIDASE FROM ASPERGILLUS NIGER

This is a continuation of copending application Ser. No. 07/575,075 filed on Aug. 30, 1990, now abandoned.

BACKGROUND OF THE INVENTION

Glucose oxidase (GOD) is an enzyme which catalyzes the following reaction:

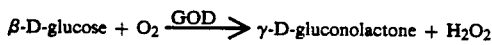

This enzyme is currently obtained mainly from Aspergillus Niger and is used in various applications such as the removal of oxygen (for example from foods) and in determination methods for glucose (in biological liquids, foods etc.). Other useful sources of GOD include Penicillium organism such as Penicillum notatum. As in the case of all enzymes, GOD is poorly stable, and therefore for commercial purposes formulations of solid or liquid type are generally used, depending on the type of application for which the enzyme is intended.

Formulations of the liquid type are easier to produce than solid formulations, but the enzyme is less stable and the preparation has therefore a shorter shelf life.

Various efforts have therefore been made in the past to overcome the drawback of excessive instability of the enzyme in liquid form. The literature on this subject includes for example Fieschl J. et al., Clin. Chem. 21, 6, 760–761 (1975), the patent CH 664,160 A5 and Boehringer Mannheim Technical Bullentin EC.1.1.3.4, proposing the use of various stabilizing substances to added to liquid GOD preparations, such as non-ionic surfactants or sodium chloride.

In addition current liquid GOD preparations generally contain a buffer in a concentration adequate to stabilize the solution pH. A phosphate buffer is the one most commonly used in reagent formulations normally employed for determining glucose in biological liquids.

SUMMARY OF THE INVENTION

The object of the present invention is to provide a method for stabilizing a glucose oxidase preparation in liquid form such that it is economical to produce, stable over time and simple to use compared with previously proposed preparations.

In this respect, the present invention relates to the preparation of glucose oxidase enzyme in liquid form which is able to produce a preparation ready for immediate use and stable with time. According to the invention, the method for stabilizing a glucose oxidase enzyme preparation in liquid form is characterized by introducing phosphate buffer into the preparation in a concentration of between 400 and 3500 mM/l. Stated differently, the present invention provides an aqueous liquid composition comprising glucose oxidase having a pH of 6.0 to 8.0 and containing phosphate at a concentration of 400 to 3500 mM/l.

DETAILED DESCRIPTION OF THE INVENTION

Figure 1:
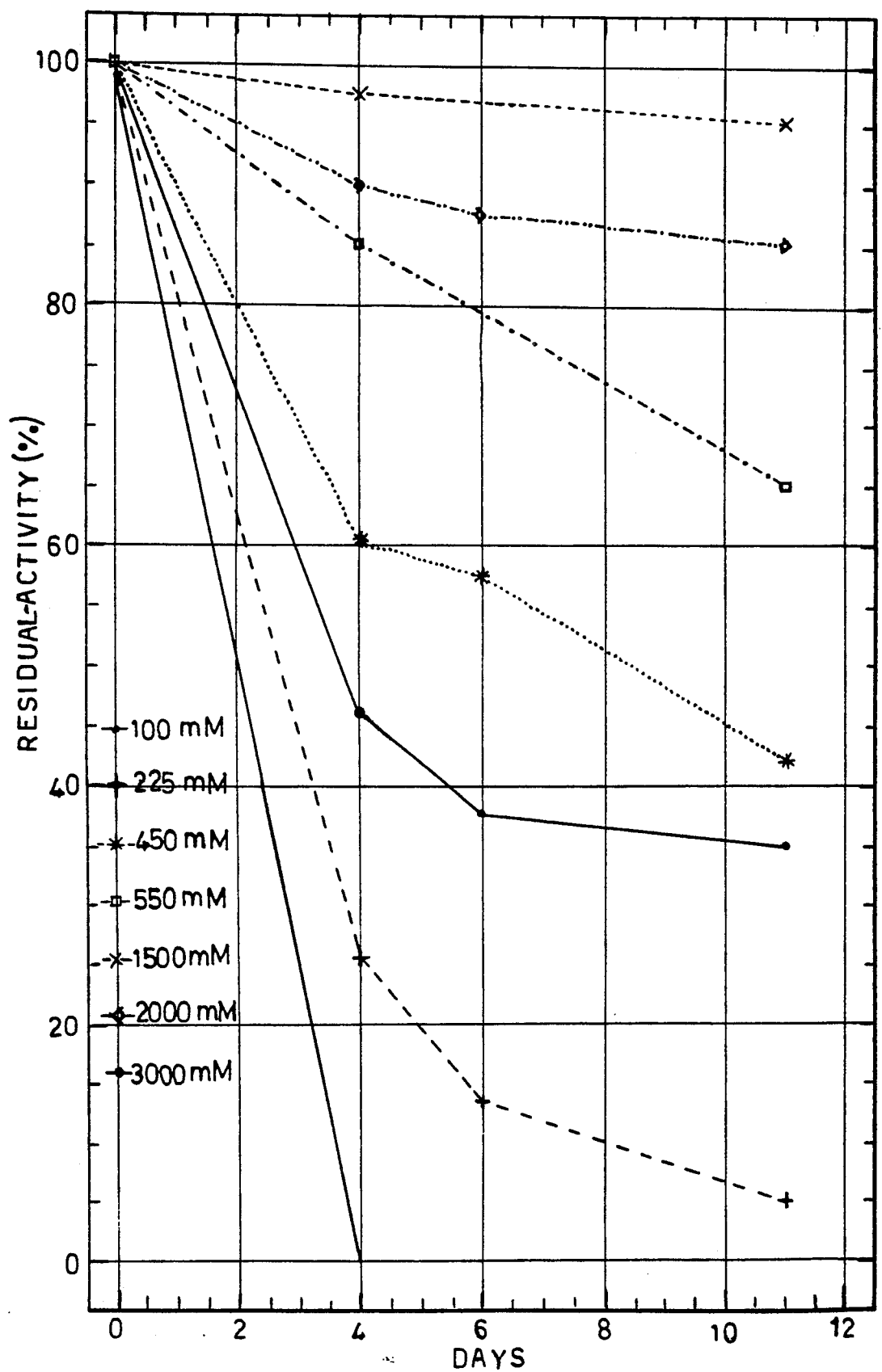

The liquid glucose oxidase preparation ready for use according to the invention is characterized by containing phosphate buffer in a concentration of between 400 and 3500 mM/l.

While potassium phosphate is preferred because of its high solubility in water, other phosphate salts or mixtures of phosphate salts, and especially sodium phosphate, may also be used. Preferred levels of phosphate are 700 to 2500 mM per liter, and especially about 1500 mM per liter.

GOD from various sources and of various concentrations can be employed. GOD from Aspergillus Niger is preferred, and concentrations in the composition of 5 to 50 IU/ml (especially 15–20 IU/ml) are preferred.

In this respect it has been surprisingly found that a phosphate buffer concentration abnormally higher than that required for it to function as a pH buffer, and in particular more than double said concentration, results in the additional and unexpected effect of stabilizing the enzyme in liquid preparations.

The stabilization effect is even more surprising as it is not related to the mere increase in the ionic force of the solution, which can be raised by adding a salt other than the phosphate buffer.

The originality of the invention resides in the fact of having identified that the phosphate buffer when used in a certain concentration range different from that normally used for buffering GOD solutions produces a pronounced stabilizing effect on the enzyme in question.

The fact that said effect depends on the use of phosphate rather than on a simple increase in ionic force or on a concentration of any buffer is demonstrated by the following observations:

1) on increasing the ionic force of a solution containing a phosphate buffer by adding a salt other than a phosphate, the stability obtained does not compare with that obtained by adding only phosphate buffer to the extent of obtaining the same ionic force; 2) a comparison with the enzyme stability in preparations using other buffers shows that the best effect is obtained with phosphate buffer.

The results of tests conducted on some liquid GOD formulations to demonstrate this important property of the preparations according to the invention using phosphate buffer for enzyme stabilization to be identified are given hereinafter by way of example.

The experimental results are shown on the accompanying figures, in which:

FIGS. 1 to 5 represent graphs showing the experimental values obtained.

A basic liquid formulation of the following composition was used:

| | |
|---|---|
| GOD | 20,000 U |
| Sodium azide (antimicrobic) | 1 g |
| $H_2O$ to make up to | 1 liter |

Substances with buffer activity were added to this formulation (to attain pH 7.2). In general, the GOD reagent compositions of the present invention can have a pH of 6.0 to 8.0, with a pH of 7.1 to 7.3 being preferred.

The buffers used, in successive tests, were the following:

Potassium phosphate, added in respective quantities of: 100, 225, 450, 550, 1500, 2000, 3000, 5000 mM Potassium phosphate 100 mM with the addition of KCl in quantities to obtain total ionic forces equivalent to 550 and 1000 mM of phosphate buffer Tris: 550, 1500, 2000 mM All the formulations were tested by an accelerated stability test at 37 and 45 deg. C.

The results of the tests conducted to better illustrate the essential principles of the invention with the compositions containing buffers of the aforesaid type and under the aforesaid conditions are described below with reference to the accompanying figures which show these experimental results for easier understanding.

The graph of FIG. 1 shows the accelerated stability of GOD at 45 deg. C. for different phosphate buffer concentrations. The horizontal axis of the curve represents the time (in days) of determining the stability and the vertical axis the residual activity of the enzyme calculated as a percentage of its initial activity at the moment it was placed in solution, the measurement being by conventional methods.

For clarity of representation the curve corresponding to the 5000 mM concentration is omitted as its shape coincides with that of 100 mM curve.

This graph shows that the enzyme stabilization increases with increase in buffer concentration, reaching its maximum effect at a buffer concentration of 1500 mM, then decreasing as the buffer concentration increases beyond said maximum concentration, so demonstrating the actual stabilization of the enzyme with the compositions of the invention. The graph of FIG. 2, in which the axes represent the same units as in FIG. 1, shows the accelerated stability of GOD at the same concentrations as the preceding graph, but at 37 deg. C. This shows that the selectivity of the phosphate buffer action on the enzyme stability at this temperature is less than at 45 deg. C.

Figure 3:
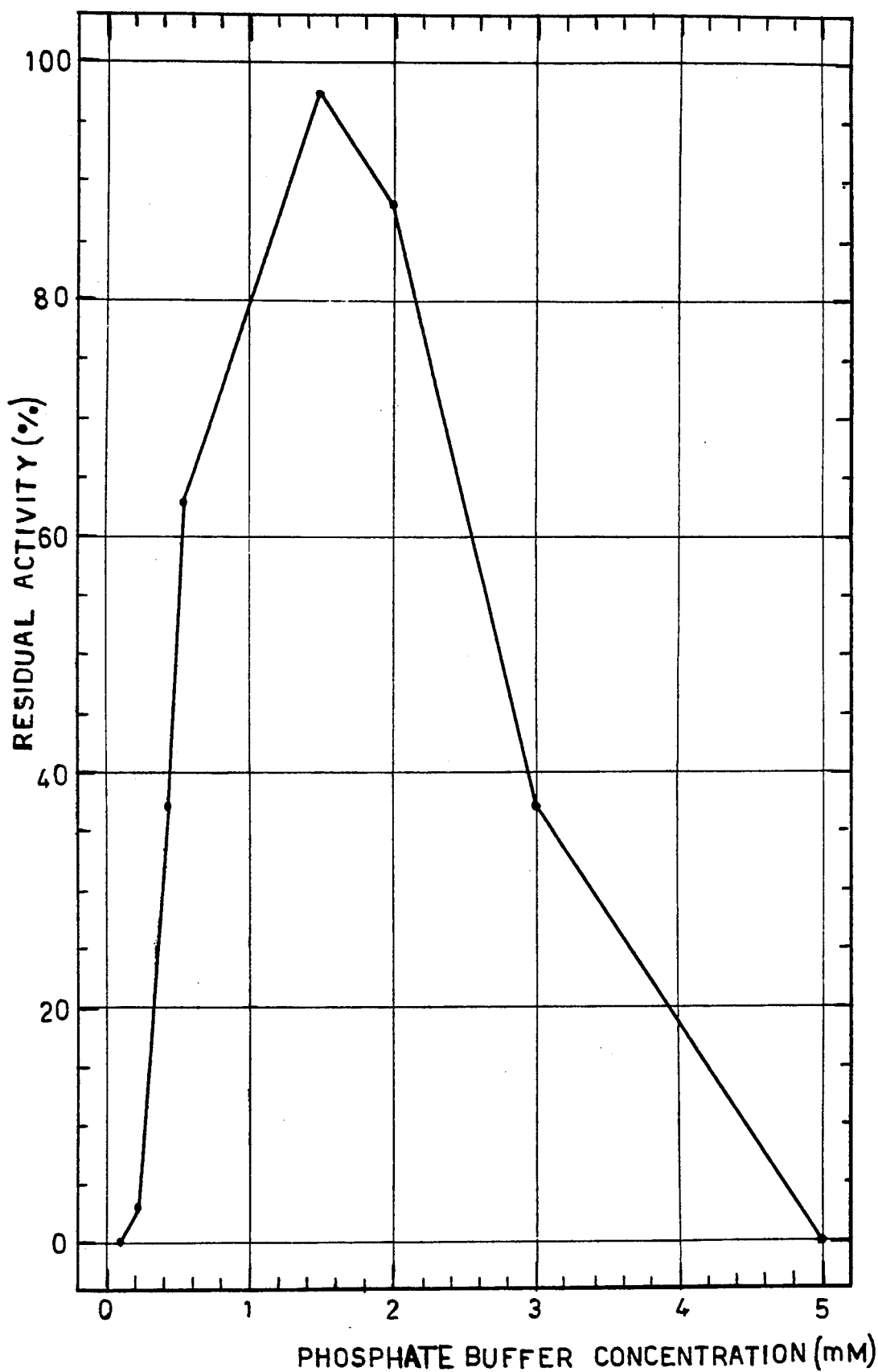

The graph of FIG. 3 is of particular importance in demonstrating the characteristics of the present invention. It shows the phosphate buffer concentration against the GOD residual activity after 13 days of storage at 45 deg. C, and is constructed from the results of the graph of FIG. 1. This graph clearly shows the existence of a buffer concentration range within which maximum enzyme stabilization surprisingly is found.

Figure 2:
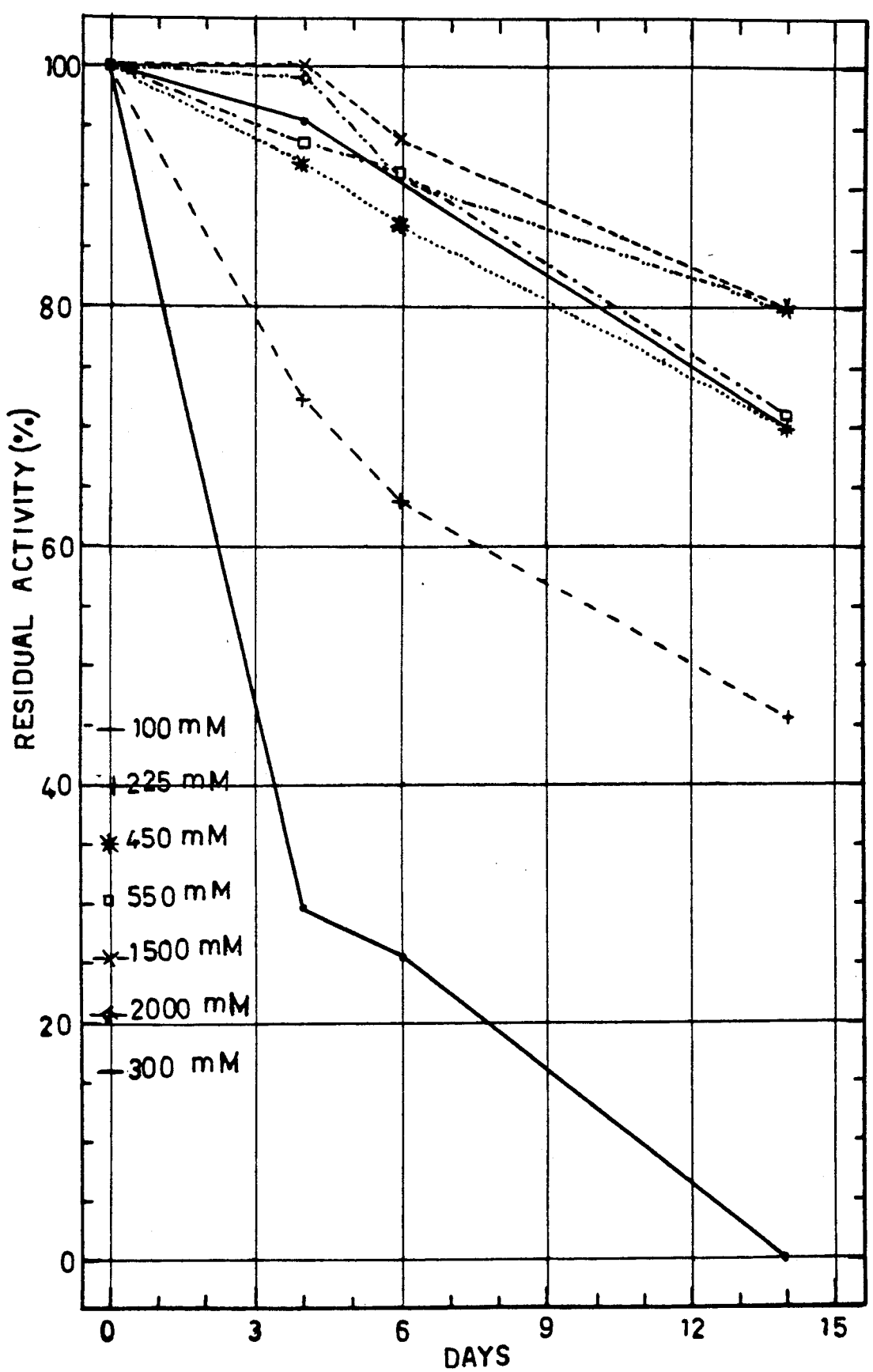
Figure 4:
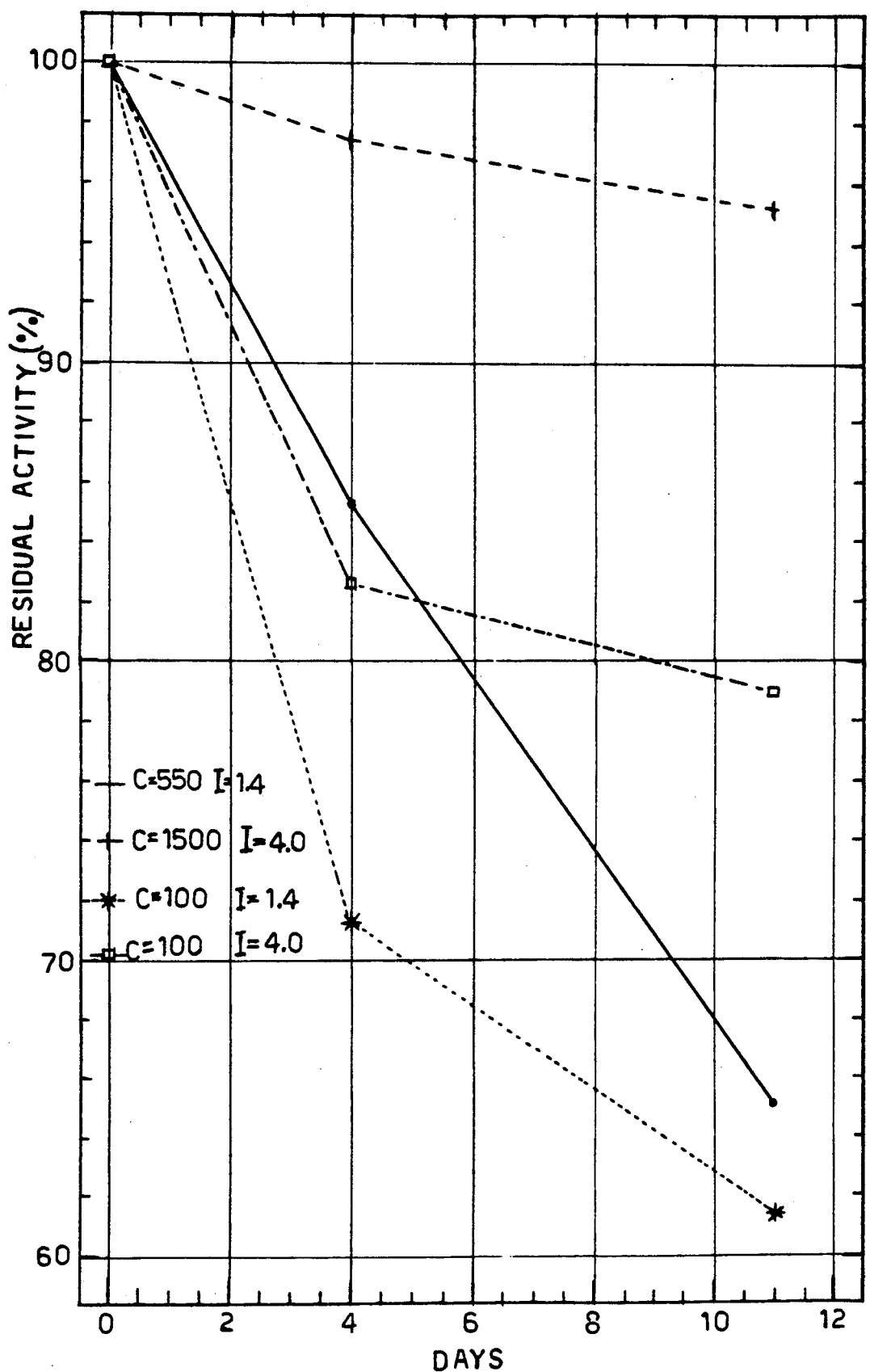

The graph of FIG. 4, in which the axes have the same meanings as the graphs of FIGS. 1 and 2, shows the results obtained with a phosphate buffer of 100 mM concentration to which potassium chloride has been added in a qunatity to raise the ionic force (I) of the final solution to two values, namely 1.4 and 4. These buffers have the same ionic force as the phosphate buffers of 550 mM and 1500 mM respectively (the two curves for 550 mM and 1500 mM phosphate from FIG. 1 are reproduced in FIG. 4). The influence of the phosphate buffer+KCl at the two stated concentrations in maintaining the GOD activity can be easily compared with that of the phosphate buffer alone at concentrations giving the same ionic strength.

It is clear from this comparison that the stabilizing effect on the enzyme depends effectively on the presence of the phosphate buffer, and that buffer solutions of equal ionic force but with a smaller phosphate buffer concentration demonstrate a considerably less effective stabilizing effect.

Figure 5:
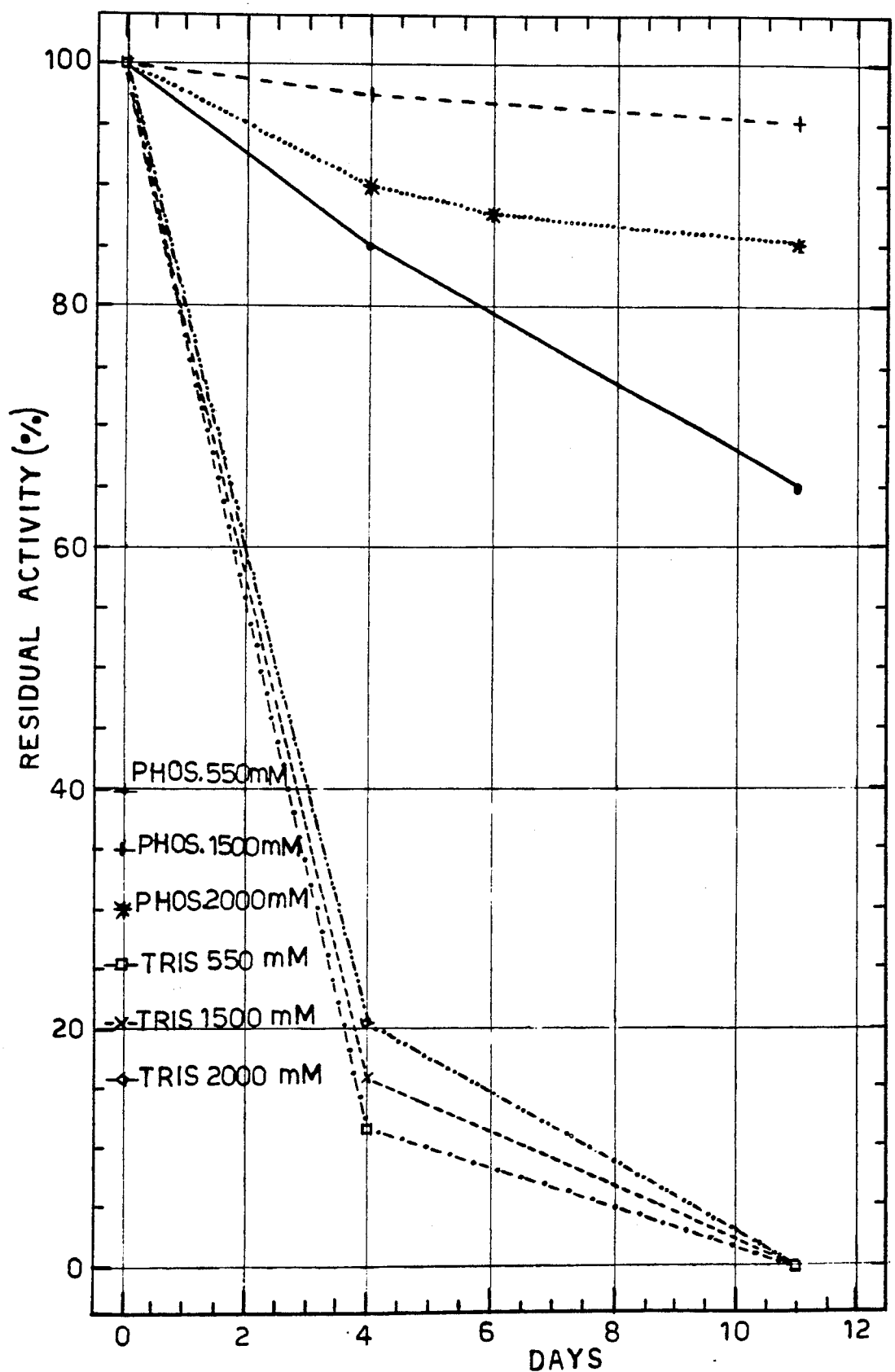

Finally the graph of FIG. 5, with the same axes as FIG. 4, compares the accelerated stability at 45 deg. C of GOD in phosphate buffer and in Tris buffer, both used at three equal concentration levels.

It is apparent that, for equal concentrations, the phosphate buffer demonstrates a stabilizing effect which is much greater than the Tris buffer.

The stabilization of glucose oxidase by the described method is particularly useful in preparing liquid preparations ready for use in determining glucose in biological liquids, and in particular for determining glucose by the so-called Trinder method.

An example of such use is as follows. First a composition was prepared with 15 U/ml of GOD from *Aspergillus niger*, and 500 to 1000 mM/l provided as potassium dihydrogen phosphate and dipotassium hydrogen phosphate (in ratios giving a final pH of 7.2), with the balance water. To this solution was added a Trinder reagent (45 mM phenol, 7.5 mM 4-amino antipyrine, 42 U/ml peroxidase and 92 mM sodium azide as microbial agent in water) at a 1 (Trinder Reagent):5 volume ratio. To 100 ul of this mixture was added (by mixing on a centrifugal analyzer) 3 ul of the sample (typically serum or urine) whose glucose concentration was to be measured and 140 $\mu$l of water. Absorbence of the reaction mixture between 500 and 520 mm was measured continuously by the spectrophotometric system of the analyzer and compared, either on an end point or fixed time point basis, to similar analyses of calibrators having known glucose concentrations.

The Trinder reagent used can be provided as a lyophillized solid or as a liquid-stable composition preferably stabilized as in Italian patent 21591 A/89 and its counterpart patent application, filed herewith and commonly-assigned. The total dilution of sample can vary from 1:80 to 1:200 by various proportions of GOD reagent and Trinder reagent. Reaction preferably occurs at about 37 deg. C., but other reaction conditions are suitable.

Furthermore, the stabilized GOD compositions of the present invention can be used with development reagents other than Trinder reagent and with hydrogen peroxide detection methodologies other than spectrophotometric, all as known to the art.

We claim:

1. An aqueous liquid composition comprising stabilized glucose oxidase having a pH of from about 6.0 to about 8.0 and containing phosphate at a concentration of 1500 to 2500 mM/l wherein said glucose oxidase retains at least 80% of its activity after 10 days at 37° C.

2. The aqueous liquid composition of claim 1 wherein the glucose oxidase is derived from *Aspergillus niger* and the pH is from about 7.1 to about 7.3.

3. The aqueous liquid composition of claim 1 wherein the pH is from about 7.1 to about 7.3.

4. The aqueous liquid composition of claim 1 wherein the glucose oxidase has a concentration of from about 5 to about 50 IU/ml.

* * * * *